(12) United States Patent
Shaw

(10) Patent No.: US 7,292,150 B2
(45) Date of Patent: Nov. 6, 2007

(54) PATIENT MONITORING SYSTEM

(76) Inventor: Mark Shaw, 1175 W. Calla Rd., B204, Poland, OH (US) 44514

(*) Notice: Subject to any disclaimer, the term of this patent is extended or adjusted under 35 U.S.C. 154(b) by 447 days.

(21) Appl. No.: 11/112,466

(22) Filed: Apr. 22, 2005

(65) Prior Publication Data

US 2006/0036136 A1 Feb. 16, 2006

Related U.S. Application Data

(60) Provisional application No. 60/564,368, filed on Apr. 22, 2004.

(51) Int. Cl.
*G08B 23/00* (2006.01)
*G08B 13/12* (2006.01)
*A61B 5/00* (2006.01)

(52) U.S. Cl. ............... 340/573.1; 340/548; 340/568.4; 340/286.07; 24/342.1

(58) Field of Classification Search ............ 340/573.1, 340/539.12, 568.4, 286.07
See application file for complete search history.

(56) References Cited

U.S. PATENT DOCUMENTS

| 4,228,426 A | * | 10/1980 | Roberts | 340/573.4 |
| 4,858,622 A | * | 8/1989 | Osterweil | 600/595 |
| 5,046,222 A |   | 9/1991 | Byers et al. | 24/343 |
| 5,066,943 A | * | 11/1991 | Demirel et al. | 340/573.4 |
| 5,276,432 A |   | 1/1994 | Travis | 340/573 |
| 5,408,213 A | * | 4/1995 | Ungarsohn | 340/427 |
| 5,767,774 A | * | 6/1998 | Wright et al. | 340/573.4 |
| 6,239,704 B1 | * | 5/2001 | Olson | 340/573.1 |

* cited by examiner

*Primary Examiner*—Donnie L. Crosland
(74) *Attorney, Agent, or Firm*—Hahn Loeser + Parks LLP; Shannon V. McCue

(57) ABSTRACT

A method is described for attaching a monitoring device to a patient comprising providing a fastener having a frame defining an opening adapted to receive a reel in a button hole fashion; inserting the reel behind a portion of the patient's clothing; positioning the frame on the opposite side of the portion of the patient's clothing relative to the reel and inserting the reel into the opening trapping the portion of material between the reel and the frame; and attaching the monitoring device to the fastener by a tether.

19 Claims, 1 Drawing Sheet

PATENT MONITORING SYSTEM

RELATED PATENT APPLICATIONS

This application claims priority from U.S. provisional application Ser. No. 60/564,368 filed Apr. 22, 2004, which is hereby incorporated by reference in its entirety.

BRIEF DESCRIPTION OF THE DRAWINGS

For a complete understanding of the objects, techniques and structure of the invention, reference should be made to the following detailed description and accompanying drawings wherein.

SUMMARY OF THE INVENTION

Figure 1:
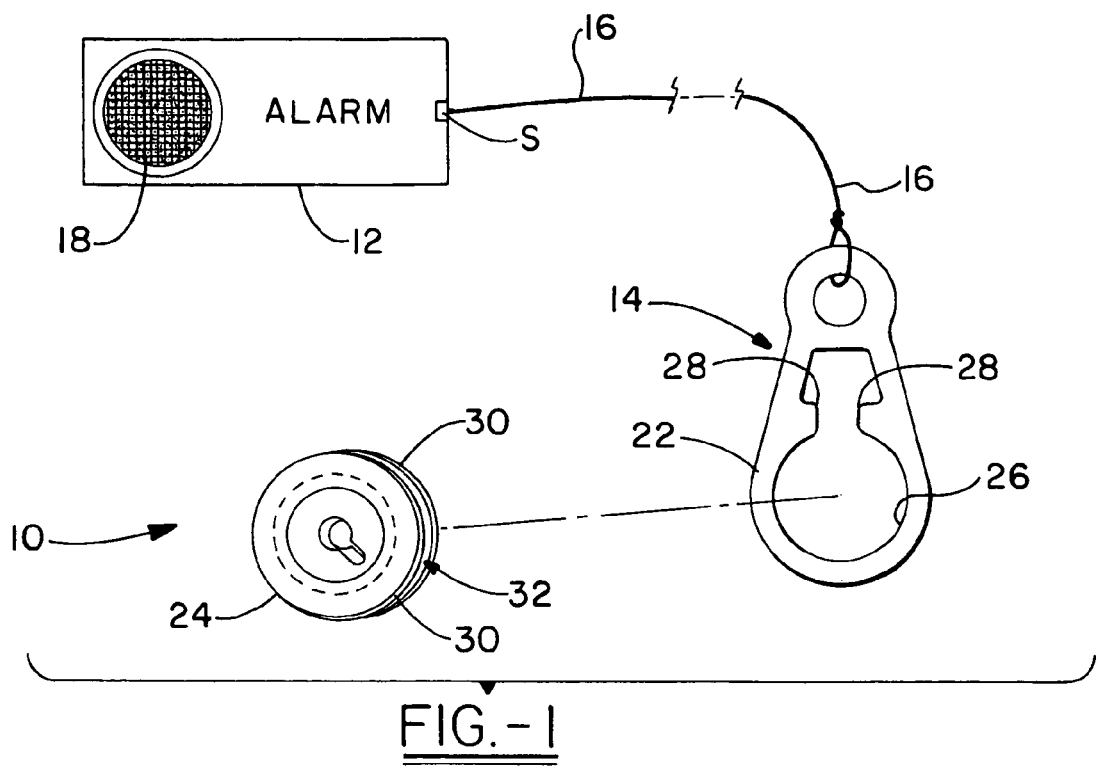
FIG. 1 is a partially schematic partially exploded view of a patient monitoring system according to the concepts of the present invention.

The invention generally provides a method of attaching a monitoring device to a patient comprising providing a fastener having a frame defining an opening adapted to receive a reel in a button hole fashion; inserting the reel behind a portion of the patient's clothing; positioning the frame on the opposite side of the portion of the patient's clothing relative to the reel and inserting the reel into the opening trapping the portion of material between the reel and the frame; and attaching a tether extending from the monitoring device to the fastener.

The invention further generally provides a patient alarm system comprising a monitoring device; a snap fastener; and a tether, wherein the tether extends from the monitoring device to the snap fastener, and wherein the snap fastener comprises a frame defining an opening adapted to receive a reel in a button hole fashion.

DETAILED DESCRIPTION OF THE INVENTION

A patient alarm system, generally indicated by the numeral 10, is depicted in the accompanying drawings. System 10, generally includes a monitoring device, a snap fastener, generally indicated by the numeral 14, and a tether 16 connecting the snap fastener to the monitoring device. The monitoring device may be an alarm 12 or nurse's station. Alternatively, the monitoring device may be a measuring device, or some combination of alarm, signal-generating unit, and measuring device. Thus reference to any one of these devices or generally to a monitoring device will be understood to collectively refer to these devices.

The alarm 12 may be one of any available alarm systems in the art and, therefore, will only generally be described. The alarm 12 includes an indicator 18, which may provide an audible alarm or visual alarm or some other cue. The alarm 12 may also send a signal to a remote nurse's station to alert care giving personnel of a condition that requires their attention. The alarm 12 may be incorporated into other equipment typically used in a patient care setting.

The alarm 12 may be used to warn a caregiver when a patient has fallen or otherwise leaves their bed. The snap fastener 14 is attached to the patient's clothing and the tether 16 extends between the snap fastener 14 and the alarm 12. The tether 16 attaches to a switch S, for example, a magnetic switch activates the alarm 12 at a selected tension. In this way, if the patient moves outside of the permitted distance provided by the cable or pulls on the cable, the alarm 12 alerts the patient's care giver.

Presently, to attach the tether 16 to the patient's clothing 20, spring loaded clips, such as, "alligator" clips, are used. The existing clips are metal and include spring-loaded jaws arranged in a scissor-like fashion. They are typically small and have relatively sharp gripping surfaces. While these clips are useful in that they are easily attached to the patient's clothing, they are just as easily removed by patients wanting to leave the bed without setting off an alarm. Oftentimes, these clips will be disengaged by accident or tear-away from the patient's clothing.

In contrast, the alarm system 10 incorporates a snap fastener 14, similar to the one described in U.S. Pat. No. 5,046,222, which is incorporated herein by reference, to attach the tether 16 to the patient's clothing 20. In general, snap fastener 14 may be more difficult for a patient to remove, and has rounded surfaces that reduce the likelihood of it tearing a patient's clothing 20. In terms of structure, snap fastener 14, generally includes a frame 22 and a reel 24, where the reel 24 is insertable within an opening 26 defined by the frame 22 and a pair of projections 28 that extend inwardly from the frame 22. Reel 24 has a pair of flanges 30 that are axially spaced from each other defining a recessed groove, generally indicated at 32 therebetween. The flanges 30 are of greater diameter than the opening 26, such that, the reel 24 must be inserted in a button-hole-like fashion. For example, the reel 24 and frame 22 may be held at an angle allowing insertion of one flange 30 through opening 26, such that, a portion of the frame 22 falls into the groove 32. At this point, the portion of the frame 22 residing within the groove 32 may be used as a fulcrum to provide the leverage necessary to stretch the frame 22 over the flange 30 of the reel 24, as the reel 24 is rotated toward a fully inserted position, where the frame 22 resides between flanges 30. Once inserted, the flanges 30 prevent axial release of the reel 24 and release requires stretching of the frame 22 over the flanges 30. As a result, relative to the alligator clips used in the art, a much larger force is required to detach the snap fastener 14.

The snap fastener 14 is preferably made of a plastic material. As shown, the snap fastener 14 has smooth surfaces that prevent it from snagging or tearing clothing as is common with the metal alligator clips used in the art.

Figures 2, 3:
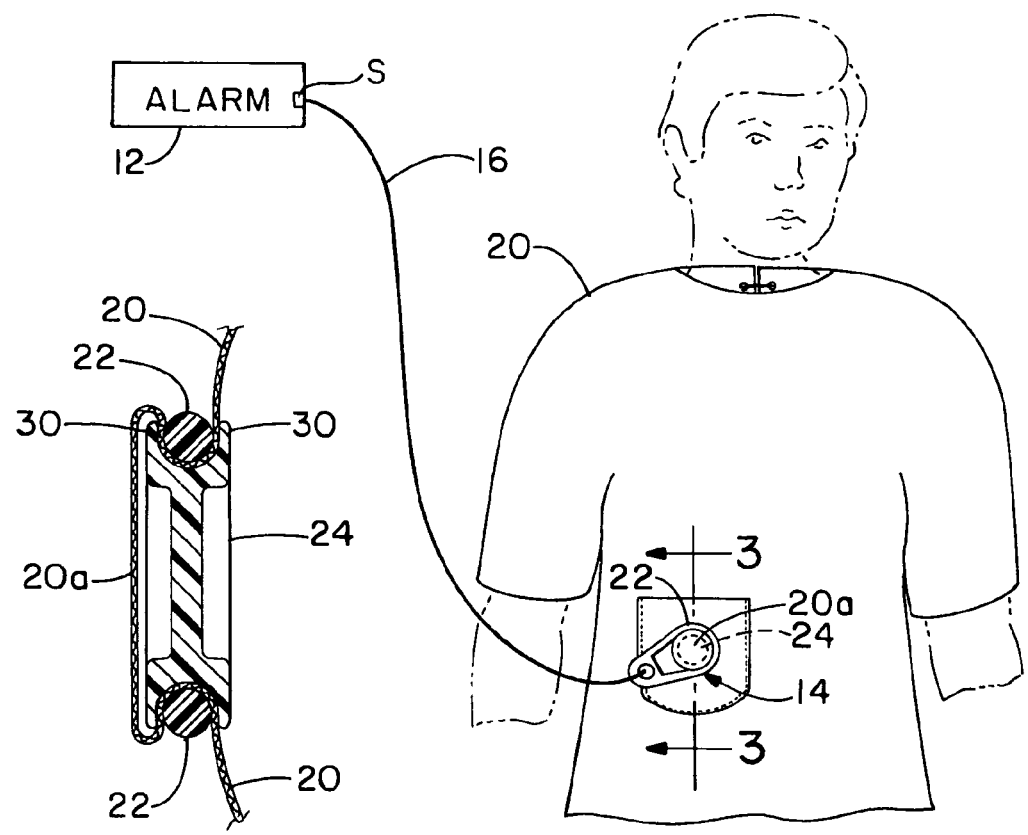
FIG. 2 is a partially schematic view of the patient monitoring system depicting a method of attaching a patient monitoring system to a patient according to the concepts of the present invention.
FIG. 3 is a sectional side elevational view as might be seen along line 3-3 in FIG. 2.

As best shown in FIGS. 2 and 3, according to the concepts of the present invention, snap fastener 14 is attached to a patient's clothing 20, according to the following steps. The reel 24 is inserted within the patient's clothing 20, such that, the reel 24 is covered by a portion of clothing 20A on one side. A patient's pocket may be used for this purpose, without placing the fastener against the patient's skin. With the portion 20A of clothing 28 covering the reel 24, the care giver holds the reel 24 and places the frame 22 over the portion 20A of clothing 20 and with the portion 20A still covering the reel 24 inserts the reel 24 within the opening 26 of frame 22, in the manner described above. As best shown in FIG. 3, the portion 20A of clothing 20 is wrapped around the reel 24 and trapped between the frame 22 and reel 24. The tether 16 may be attached to the frame 22 before attaching the fastener 14 or after the fastener 14 has been attached to the patient's clothing 20. In the example shown, the tether 16 is attached to an alarm 12 to monitor the patient. As described above, with the tether 16 attached, selected movement of the patient causes the tether 16 to set off the alarm 12 and alert the care giver of a condition that requires their attention.

Within the care giving setting, it is often necessary to attach other monitoring devices, for example, a pulseoximeter, to the patient. At times, these devices may be dislodged and fall off of the patient, oftentimes to the floor. According to another aspect of the present invention, such monitoring devices are attached to the patient's clothing 20, such that, if they become dislodged they will not be lost or fall to the floor. The monitoring device would be attached to a tether 16 having a fastener 14 tied to the opposite end of the tether. The fastener 14 would then be attached to the patient's clothing 20 according to the steps described above. In this way, if the monitoring device fell or was dislodged from the patient's clothing, the tether 16 would prevent the monitoring device from falling to the floor and could be used in locating the device.

In light of the foregoing, it should thus be evident that a patient monitoring system according to the concepts of the present invention substantially improves the art. While, in accordance with the patent statutes, a preferred embodiment of the present invention has been described in detail hereinabove, the present invention is not to be limited thereto or thereby. It will be appreciated that various modifications may be made to the above-described embodiment without departing from the spirit of the invention. Therefore, to appreciate the scope of the invention, reference should be made to the following claim.

What is claimed is:

1. A method of attaching a monitoring device to a patient comprising:
   providing a fastener having a frame defining an opening adapted to receive a reel in a button hole fashion;
   inserting the reel behind a portion of the patient's clothing;
   positioning the frame on the opposite side of the portion of the patient's clothing relative to the reel and inserting the reel into the opening trapping the portion of material between the reel and the frame; and
   attaching the monitoring device to the fastener by a tether.

2. The method of claim 1, wherein the monitoring device includes an alarm, nurse's station, or measuring device.

3. The method of claim 1, wherein the monitoring device includes an alarm.

4. The method of claim 3, wherein the alarm includes an indicator adapted to signal a caregiver.

5. The method of claim 4, wherein the indicator includes an audible tone or a visual cue.

6. The method of claim 4, wherein the alarm is adapted to send electronic signals to a nurse's station.

7. The method of claim 1, wherein the monitoring device comprises a switch, and wherein the tether is attached to the switch.

8. The method of claim 1, wherein said step of attaching the tether is accomplished before said step of positioning the frame.

9. The method of claim 1, wherein said step of inserting the reel includes placing the reel inside a pocket on the patient's clothing.

10. A patient alarm system comprising:
    a monitoring device;
    a snap fastener; and
    a tether, wherein the tether extends from the monitoring device to the snap fastener, and wherein the snap fastener comprises a frame defining an opening adapted to receive a reel in a button hole fashion.

11. The system of claim 10, wherein the monitoring device includes an alarm.

12. The system of claim 10, wherein the alarm includes an indicator adapted to signal a caregiver.

13. The system of claim 12, wherein the indicator is selected from an audible tone or a visual cue.

14. The system of claim 10, wherein the monitoring device includes a nurse's station.

15. The system of claim 12, wherein the alarm is adapted to send electronic signals to a nurse's station.

16. The system of claim 10, wherein the monitoring device includes a measuring device.

17. The system of claim 16, wherein the measuring device is a pulseoximeter.

18. The system of claim 10, wherein the opening is defined by the frame and a pair of projections that extend inwardly from the frame.

19. The system of claim 10, wherein the reel includes a pair of flanges that are axially spaced from each other defining a recessed groove.

* * * * *